United States Patent [19]

Laloz et al.

[11] 4,365,082
[45] Dec. 21, 1982

[54] PROCESS FOR CONVERTING OLEFINS TO UNSATURATED ESTERS, USING CATALYSTS CONTAINING PALLADIUM HYDROXAMATES

[75] Inventors: Jean P. Laloz, Marly le Roi; Hubert Mimoun, Rueil-Malmaison; Jean J. Rouxel, Longuesse; Lucien Saussine, Chatou, all of France

[73] Assignee: Institut Francais du Petrole, Rueil-Malmaison, France

[21] Appl. No.: 277,542

[22] Filed: Jun. 26, 1981

[30] Foreign Application Priority Data

Jun. 26, 1980 [FR] France ................. 80 14289

[51] Int. Cl.$^3$ .......................................... C07C 67/055
[52] U.S. Cl. ............................... 560/243; 252/431 C; 252/431 N
[58] Field of Search ............................... 560/243, 245

[56] References Cited

U.S. PATENT DOCUMENTS

| 3,221,045 | 11/1965 | McKeon | 560/243 |
| 3,238,247 | 3/1966 | McKeon | 560/243 |
| 3,450,748 | 6/1969 | Schaeffer | 560/243 |
| 3,578,698 | 5/1971 | Hayden | 560/243 |
| 3,609,180 | 9/1971 | Shigematsu | 560/243 |
| 3,822,308 | 7/1974 | Kronig | 560/245 |
| 3,906,036 | 9/1975 | Dirks | 560/243 |
| 3,960,930 | 6/1976 | Clark | 560/243 |
| 4,161,160 | 7/1979 | Klass | 560/243 |

Primary Examiner—Michael L. Shippen
Attorney, Agent, or Firm—Millen & White

[57] ABSTRACT

Olefins are oxidized to unsaturated esters by means of molecular oxygen in the presence of a carboxylic acid and an organometallic palladium complex containing two identical or different hydroxamate anions or one hydroxamate anion and a carboxylate anion, said complex acting as catalyst.

23 Claims, No Drawings

PROCESS FOR CONVERTING OLEFINS TO UNSATURATED ESTERS, USING CATALYSTS CONTAINING PALLADIUM HYDROXAMATES

BACKGROUND OF THE INVENTION

This invention concerns the production of unsaturated esters by oxidation of olefins with molecular oxygen in the presence of at least one carboxylic acid in homogeneous phase, the catalyst being an organo-metallic complex of palladium containing two identical or different hydroxamate anions or one hydroxamate anion and one carboxylate anion.

The invention provides in particular for the conversion of ethylene to vinyl acetate according to the equation:

$$CH_2=CH_2 + CH_3CO_2H + \tfrac{1}{2}O_2 \rightarrow CH_2=CH-OCOCH_3 + H_2O$$

or the conversion of propylene to allyl acetate according to the equation:

$$CH_3-CH=CH_2 + CH_3CO_2H + \tfrac{1}{2}O_2 \rightarrow CH_2=CH-CH_2-OCOCH_3 + H_2O$$

or the conversion of isobutene to methallyl acetate according to the equation:

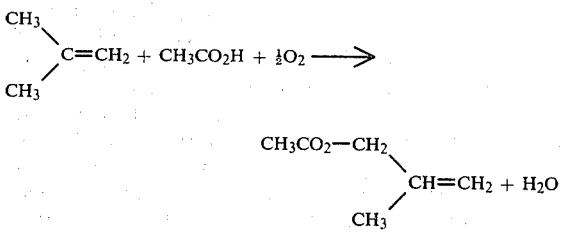

The presently existing processes which operate in homogeneous liquid phase and provide for the conversion of ethylene to vinyl acetate, generally make use of an acetic solution containing alkali ions, copper ions, and acetate ions and chlorine ions as well as bivalent palladium salts. This technique has been used in processes described in many patents, particularly in the British Pat. No. 964,001 and the U.S. Pat. No. 3,260,739.

The chlorine ions have a decisive action for regenerating bivalent palladium and prevent its precipitation from the medium as palladium metal. However these catalytic solutions containing chlorine ions in acetic medium are responsible for a substantial corrosion of stainless steel and the formation of chlorinated products which are difficult to remove. On the other hand, as stated in the U.S. Pat. No. 3,906,036, a substantial portion of copper is converted to copper oxalate which is insoluble in the acetic medium and is catalytically inactive.

Catalytic systems operating in the absence of halide ions have been suggested, particularly in the U.S. Pat. No. 3,238,247, but they have only a very limited life time.

Most of the existing processes providing for the conversion of ethylene to vinyl acetate are operated in heterogeneous phase in the presence of a catalyst containing palladium deposited on an inorganic carrier such as silica or alumina and in the presence of promoters such as alkali or alkaline earth metal salts of carboxylic acids. This is described, for example, in the U.S. Pat. No. 3,822,308. However, these processes in heterogeneous phase are conducted at high temperature and produce a non-negligible amount of $CO_2$. Moreover, they yield a relatively low production and require a periodic regeneration of the catalyst.

One of the advantages of the process according to the present invention is to proceed in the liquid phase in the complete absence of halide ions. Another advantage of the process consists in the fact that it provides, for example, for the production of vinyl acetate from ethylene and of allyl acetate from propylene with high velocity and selectivity under moderate temperature conditions.

DETAILED DISCUSSION

The catalyst, according to the invention, consists of an organometallic complex of palladium having the general formula PdAA' wherein A is a hydroxamate anion and A' is a hydroxamate anion or a carboxylate anion.

The anion A is a hydroxamate anion of the general formula

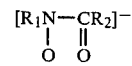

wherein $R_1$ and $R_2$, which are identical or different, each represent an alkyl, aryl, aralkyl, cycloalkyl or alkylaryl radical containing 1 to 20 carbon atoms. $R_1$ is preferably an aromatic radical, either substituted or not, or a group linked to N at a tertiary carbon carrying three substituents which are alkyl radicals, identical or not, or which form together an aryl radical, so that no hydrogen atom is preferably present on the carbon adjacent to the nitrogen atom of the hydroxamate anion. $R_2$ is a substituted or unsubstituted alkyl or aryl group.

The anion A' is a hydroxamate, identical or not to A, but defined in the same way as said anion A, or is a carboxylate anion such as, for example, an acetate, a trichloroacetate or a trifluoroacetate.

Non-limitative examples of compounds of formula PdAA' which can be used according to the invention are the following complexes:
Palladium N-phenylbenzohydroxamate (A=A', $R_1=R_2=$Phenyl), palladium N-phenyltrifluoroacetohydroxamate (A=A', $R_1=$Phenyl, $R_2=CF_3$), palladium N-tert.butylbenzohydroxamate (A=A', $R_1=$tert.butyl, $R_2=$Phenyl), palladium N-tert.butylacetohydroxamate (A=A', $R_1=$tert.butyl, $R_2=$methyl), palladium N-parafluorophenylbenzohydroxamate (A=A', $R_1=$parafluorophenyl, $R_2=$phenyl), palladium N-parafluorophenylacetohydroxamate (A=A', $R_1=$parafluorophenyl, $R_2=$methyl), palladium N-phenyl paranitrobenzohydroxamate (A=A', $R_1=$phenyl, $R_2=$paranitrophenyl), palladium N-parafluorophenyl paranitrobenzohydroxamate (A=A', $R_1=$parafluorophenyl, $R_2=$paranitrophenyl), palladium N-phenyl 2,6-dichlorobenzohydroxamate ($R_1=$phenyl, $R_2=$2,6 dichlorophenyl), palladium N-phenyl 2,6-dimethoxybenzohydroxamate ($R_1=$phenyl, $R_2=$2,6 dimethoxyphenyl), palladium N-t-butyl-p-phenylbenzohydroxamate, palladium N-t-butyl 2,6-dimethoxybenzohydroxamate, palladium N-t-butyl 2,6-dichlorobenzohydroxamate, palladium N-parafluorophenyl, 2,6-dimethoxybenzohydroxamate, palladium N-parafluorophenyl 2,6-dinitrobenzohydroxamate, palladium N-phenyl benzohydroxamate acetate (A'=acetate, A=hydroxamate), palladium trifluoroacetate N-tertbutylbenzohydroxamate (A'=trifluoroacetate, A=hydroxamate), palladium N-tertbutylbenzohydroxamate acetate (A'=acetate, A=hydroxamate), etc.

Most of the complexes used according to this invention are new and are generally prepared by adding one or two equivalents of hydroxamic acid, as above defined, to the palladium salt or complex in solution in an organic solvent such, for example, as methylene chloride or tetrahydrofuran.

These complexes may also be prepared in situ by introducing the hydroxamic acid into the reaction solution containing the palladium salt.

One of the advantages of using palladium hydroxamates is that the latter are generally sufficient to catalyse alone the conversion of olefins to esters with a high velocity and a high selectivity.

The complex concentration in the medium is generally from 0.005 to 0.5 mole per liter, and preferably 0.01 to 0.1 mole per liter.

It may be advantageous, in order to increase the catalyst stability, to add to the palladium hydroxamate a cocatalyst selected from an acetate or a hydroxamate of a transition metal, such for example as iron, copper, cobalt or manganese. Copper acetate or hydroxamate (e.g. copper N-phenylbenzohydroxamate) is however preferred and may be used in amounts from 1 to 100 moles per gram-atom of palladium, said proportions being also applicable in the case of the acetates or hydroxamates of other metals.

In addition to the two above-mentioned metal constituents, it may also be advantageous, in order to improve the activity of the catalytic system, to add a carboxylate of an alkali or alkaline-earth metal such, for example, as lithium, sodium, potassium and barium.

The alkali or alkaline earth metal carboxylate concentration is in the range from 0 to 4 moles per liter and preferably from 0.15 to 2 moles per liter of reaction medium.

When using simultaneously, in addition to the catalyst according to the invention, a co-catalyst such as a copper acetate or hydroxamate and an alkali or alkaline earth metal carboxylate, it is generally preferable that the molar catalyst concentration according to the invention be from 0.0005 M to 1 M and preferably from 0.002 to 0.05 M with respect to the total catalyst solution containing copper acetate or hydroxamate and alkali or alkaline earth metal carboxylate.

The reaction temperature is generally from 30° to 200° C., more particularly from 80° to 180° C.

The reaction is conducted in the liquid phase at pressures generally from 2 to 100 bars, preferably from 3 to 50 bars.

The oxidizing gas is oxygen, used either pure or diluted with an inert gas, for example with nitrogen, as air. It may also be advantageous to make use of a gaseous diluent such as ethane or methane.

The catalyst system may be regenerated in the reaction medium itself by introducing a molecular oxygen containing gas in the absence of halide ions.

The invention is illustrated by the following non-limitative examples.

EXAMPLE 1

Preparation of palladium N-phenyl benzohydroxamate:

1.35 g (6 mmoles) of palladium acetate are dissolved in 80 cc of distilled tetrahydrofuran; 2.56 g (12 mmoles) of N-phenylbenzohydroxamic acid are then added and the temperature is maintained at 20° C. for 4 hours; after evaporation of the solvent, the obtained brick-red solid is recrystallized in a mixture of methylene chloride with ether. There is thus obtained 2.9 g (90%) of palladium N-phenylbenzohydroxamate.

The other palladium complexes used hereinafter and containing hydroxamates ligands are synthesized in the same operating manner.

EXAMPLE 2

180 cc of acetic acid, 1 mmole of palladium N-phenylbenzohydroxamate and 4.1 g of sodium acetate are introduced into a stainless steel reactor. The mixture is heated to 100° C.; there is then introduced 0.15 mole of ethylene; the pressure reaches 13 bars and oxygen is immediately introduced in order that the molar ratio of ethylene to oxygen does not exceed 9.5:1. The total pressure is maintained constant by injection of ethylene and oxygen. After 3 h 30 of reaction, the reaction mixture is cooled down and degased; a chromatographic analysis shows the formation of 0.2 mole of vinyl acetate and 0.008 mole of acetaldehyde.

The vinyl acetate selectivity is 96%.

EXAMPLE 3

The operation is conducted as in example 1, except that there is also added 1.1 mmole of copper N-phenylbenzohydroxamate to the reaction mixture. After 3 h 30 of reaction, there is obtained 0.24 mole of vinyl acetate and 0.0072 mole of acetaldehyde. The vinyl acetate selectivity is 97%; this example shows that the addition of copper N-phenylbenzohydroxamate results in increased velocity and selectivity.

EXAMPLES 4 TO 7

The operation is conducted as in example 1 in 180 cc of acetic acid containing 4.1 g of sodium acetate. Various catalysts are used, optionally in the presence of a cocatalyst.

| EXAMPLE No. | DURATION (hours) | PALLADIUM COMPLEX (mmoles) | COPPER SALT (mmoles) | VINYL ACETATE (mole) | ACETALDEHYDE (mole) | SELECTIVITY % |
|---|---|---|---|---|---|---|
| 4 | 3 H 30 | (ph-N—CCF$_3$)$_2$Pd  \|  \|\|  O  O  1 mmole | — | 0.107 | 0.004 | 96.4 |
| 5 | 3 H 15 | (ph-N—CCF$_3$)$_2$Pd  \|  \|\|  O  O  1 mmole | Cu(OAc)$_2$, H$_2$O  5 mmoles | 0.149 | 0.0064 | 95.9 |

| EXAMPLE No. | DURATION (hours) | PALLADIUM COMPLEX (mmoles) | COPPER SALT (mmoles) | VINYL ACETATE (mole) | ACETALDEHYDE (mole) | SELECTIVITY % |
|---|---|---|---|---|---|---|
| 6 | 3 H 30 | (t-BuN—C—ph)$_2$Pd  \| \|\|  O  O  1 mmole | — | 0.04 | 0.0014 | 96.6 |
| 7 | 3 H 15 | (t-BuN—C—ph)$_2$Pd  \| \|\|  O  O  1 mmole | (t-BuN—C—ph)$_2$Cu  \| \|\|  O  O  1 mmole | 0.063 | 0.0026 | 96 |

Ac = acetate;
ph = phenyl
t-Bu = tert-butyl.

EXAMPLE 8

The operation is conducted as in example 1, but with the use of one millimole of copper acetate to which are added 3 mmoles of N-phenylbenzohydroxamic acid; after 3 hours of reaction, there is obtained 0.16 mole of vinyl acetate; the selectivity is 96.5%.

EXAMPLE 9

The operation is conducted as in example 7, except that N-phenylbenzohydroxamic acid is replaced with N-tert.butylbenzohydroxamic acid. After 3 H 30 of reaction, there is obtained 0.18 mole of vinyl acetate. The selectivity is 96%.

EXAMPLE 10

The operation is conducted as in example 1, but with the use of 1 millimole of palladium acetate and 2 millimoles of benzoyl-t-butyl nitroxide radical prepared according to the method published in J.C.S., perkin I, 1978, 1066.

After 3 H 30 of reaction, there is obtained 0.110 mole of vinyl acetate with a selectivity of 96%.

EXAMPLE 11

In a stainless steel reactor, there is introduced 50 cc of acetic acid, 0.5 millimole of palladium N-phenylbenzohydroxamate and 0.41 g of sodium acetate; the mixture is heated to 120° C. and 0.20 mole of propylene is then introduced into the reactor; the pressure reaches 18 bars and oxygen is then introduced so as to maintain a total pressure of 22 bars. After 4 hours of reaction, the chromatographic analysis shows that 0.108 mole of allyl acetate, 0.001 mole of acetone and 0.001 mole of acrolein have formed. The allyl acetate selectivity is 98%.

This example shows that the presence of the N-phenylbenzohydroxamic radical in the palladium complex catalyses the formation of allyl acetate from propylene and acetic acid, in the absence of copper.

EXAMPLE 12

Example 10 is repeated but with the use of palladium N-phenyl trifluoroacetohydroxamte. 0.104 mole of allyl acetate, 0.003 mole of acetone and 0.004 mole of acrolein have formed in 4 hours.

The selectivity to allyl acetate amounts to 93.7%.

EXAMPLE 13

The operation is conducted as in example 11, but with the further addition of 0.05 mole of copper acetate. After 1 H 30 of reaction, there is obtained 0.116 mole of allyl acetate, 0.0034 mole of acetone and 0.0036 mole of acrolein. The selectivity to allyl acetate amounts to 94.3%. This example shows that the addition of copper acetate, with a ratio Pd/Cu=1, results in an increase of the reaction velocity.

What is claimed is:

1. In a catalytic process for manufacturing an unsaturated ester by oxidizing an olefin in the presence of molecular oxygen, a carboxylic acid and a catalyst, the improvement wherein said catalyst comprises an organometallic palladium complex having the formula PdAA', wherein A is a hydroxamate anion; and A' is an identical or different hydroxamate anion or a carboxylate anion.

2. A process according to claim 1, which is effected in the absence of halide ions.

3. A process according to claim 1, wherein the hydroxamate anion A has the formula

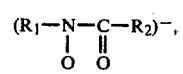

wherein R$_1$ and R$_2$ are each independently a C$_{1-20}$ alkyl, aryl, aralkyl, cycloalkyl or alkylaryl group.

4. A process according to claim 3, wherein R$_1$ is phenyl or para-fluorophenyl.

5. A process according to claim 3, wherein R$_1$ is a group linked to N at a tertiary carbon whose three substituents are independently alkyl groups or together form an aryl group.

6. A process according to claim 1, wherein the catalyst is palladium N-phenylbenzohydroxamate, palladium N-phenyltrifluoroacetohydroxamate, palladium N-tert.butylbenzohydroxamate, palladium N-tert.butylacetohydroxamate, palladium N-parafluorophenylbenzohydroxamate, palladium N-parafluorophenylacetohydroxamate, palladium N-phenyl paranitrobenzohydroxamate, palladium N-parafluorophenyl paranitrobenzohydroxamate, palladium N-phenyl 2,6-dichlorobenzohydroxamate, palladium N-phenyl 2,6-dimethoxybenzohydroxamate, palladium N-t-butyl p-phenylbenzohydroxamate, palladium N-t-butyl 2,6-dimethoxybenzohydroxamate, palladium N-t-butyl 2,6-dichlorobenzohydroxamate, palladium N-parafluorophenyl 2,6-dimethoxybenzohydroxamate, palladium N-phenyl benzohydroxamate acetate, palladium trifluoroacetate N-tert.butylbenzohydraxamate, palladium N-tert.butylbenzohydroxamate acetate or palladium N-parafluorophenyl 2,6-dinitrobenzohydroxamate.

7. A process according to claim 1, wherein the concentration of said organometallic palladium catalyst complex is from 0.005 to 0.5 mole per liter of reaction medium.

8. A process according to claim 7, wherein said catalyst concentration is from 0.01 to 0.1 mole per liter of reaction medium.

9. A process according to claim 7, which is effected in the further presence of a transition metal acetate or hydroxamate cocatalyst at a concentration of from 1 to 100 moles per gram-atom of palladium.

10. A process according to claim 9, which is effected in the further presence of an alkali or alkaline earth metal carboxylate at a concentration of from 0 to 4 moles per liter of reaction medium.

11. A process according to claim 3, wherein $R_1$ is tert-butyl.

12. A process according to claim 3, wherein $R_2$ is phenyl, methyl, para-nitrophenyl, 2,6-dichlorophenyl, 2,6-dimethoxyphenyl or 2,6-dinitrophenyl.

13. A process according to claim 1, wherein A' is acetate, trichloroacetate or trifluoroacetate.

14. A process according to claim 9, wherein said transition metal acetate or hydroxamate cocatalyst is an iron, copper, cobalt or manganese acetate or hydroxamate.

15. A process according to claim 14, wherein said cocatalyst is a copper acetate or hydroxamate.

16. A process according to claim 15, wherein said cocatalyst is copper N-phenylbenzohydroxamate.

17. A process according to claim 10, wherein the concentration of said alkali or alkaline earth metal carboxylate is from 0.15 to 2 moles per liter of reaction medium.

18. A process according to claim 10, wherein the concentration of said organometallic palladium catalyst complex is from 0.0005 to 1 mole per liter of total solution.

19. A process according to claim 18, wherein said catalyst concentration is from 0.002 to 0.05 moles per liter.

20. A process according to claim 1, wherein the reaction is effected at a temperature of 30°–200° C.

21. A process according to claim 20, wherein said temperature is 80°–180°0 C.

22. A process according to claim 1, wherein the reaction is effected at a pressure of 2–100 bar.

23. A process according to claim 22, wherein said pressure is 3–50 bar.

* * * * *